(12) United States Patent
Liu et al.

(10) Patent No.: US 10,221,423 B2
(45) Date of Patent: Mar. 5, 2019

(54) METHOD OF GENE EXPRESSION REGULATION

(71) Applicant: Jiangnan University, Wuxi (CN)

(72) Inventors: Long Liu, Wuxi (CN); Jian Chen, Wuxi (CN); Guocheng Du, Wuxi (CN); Xian Yin, Wuxi (CN); Jianghua Li, Wuxi (CN)

(73) Assignee: Jiangnan University, Wuxi (CN)

( * ) Notice: Subject to any disclaimer, the term of this patent is extended or adjusted under 35 U.S.C. 154(b) by 4 days.

(21) Appl. No.: 15/891,504

(22) Filed: Feb. 8, 2018

(65) Prior Publication Data

US 2018/0171344 A1 Jun. 21, 2018

Related U.S. Application Data

(62) Division of application No. 15/349,025, filed on Nov. 11, 2016, now Pat. No. 9,926,569.

(30) Foreign Application Priority Data

Nov. 20, 2015 (CN) .......................... 2015 1 0812316

(51) Int. Cl.
*C12N 15/80* (2006.01)
*C12N 1/14* (2006.01)
*C07K 14/38* (2006.01)
*C12N 15/63* (2006.01)

(52) U.S. Cl.
CPC .............. *C12N 15/80* (2013.01); *C07K 14/38* (2013.01); *C12N 1/14* (2013.01); *C12N 15/63* (2013.01)

(58) Field of Classification Search
None
See application file for complete search history.

*Primary Examiner* — Mindy G Brown
(74) *Attorney, Agent, or Firm* — SZDC Law P.C.

(57) ABSTRACT

The invention discloses a promoter which can be induced to express in acidic conditions, and relates to the field of bioengineering technology. The promoters of the invention are separated from *A. niger* and can actuate and/or regulate the expression of the effectively connected nucleic acids in *A. niger*. In the invention the expression of the promoters is studied in *A. niger*, and it is indicated that some promoters show weak expression, and some show strong activity. The invention provides an effective method and new thought for organic acids production by fungi or other products produced by fermentation under acidic conditions.

1 Claim, 1 Drawing Sheet
Specification includes a Sequence Listing.

METHOD OF GENE EXPRESSION REGULATION

This application is a Divisional Application of U.S. Ser. No. 15/349,025, filed on Nov. 11, 2016, which claims the benefit of Chinese Patent Application No. 201510812316.5, filed on Nov. 20, 2015, which is incorporated by reference for all purposes as if fully set forth herein.

FIELD OF THE INVENTION

The present invention relates to the field of bioengineering technology, and more particularly to a promoter induced in acidic conditions.

DESCRIPTION OF THE RELATED ART

*Aspergillus niger* is a natural cell factory platform for production of organic acids and enzymes. Meanwhile, *A. niger* is considered generally regarded as safe (GRAS) and has abroad application in future as a host strain. A traditional method for strain improvement is mutation breeding, while the non-rational work makes the screen work time-consuming and tiring, and it is not necessarily possible to screen out excellent transformants. Several genome-sequencing works of *A. niger* were finished and transcriptome data were analyzed for mechanism of organic acid production and protein secretion, providing a guide for rational design for aim-product accumulation.

There have already been many successful works on metabolic engineering of *A. niger* to improve product synthesis. The mostly used promoters are constitutive ones, including glyceraldehyde-3-phosphate dehydrogenase promoter PgpdA of *A. nidulans*, multiprotein bridging factor 1 Pmbf of *A. niger*, citrate synthase promoter PcitA of *A. niger* and pyruvate kinase promoter Ppki of *Trichoderma reesei*. All these promoters induce gene expression from cell-growth-phase, as a result may influence the cell growth.

Inducible promoters include glucoamylase promoter Pgla, xylanase promoter Pxln, Taka-amylase A promoter Pamy, alcohol dehydrogenase promoter Palc, and Tet-on system and so on. It is necessary to add specific substrate for inducing gene expression, making these promoters useful for scientific purposes but uneconomic for industrial purpose. Moreover, the expression strength of these promoters is weaker than that of the constitutive promoters. Furthermore, the Pxln is inhibited by glucose, while the strength of Pgla is influenced by glucose concentration, resulting in the instable expression in medium with glucose as a main carbohydrate.

During the organic acids production by *A. niger*, for instance citrate fermentation, the pH of medium decreases from 5.0 to below 2.0, and a pH<3 was essential for citrate synthesis. In order to limit gene expression during cell-growth-stage but increase expression level during product accumulation stage, it is valuable to find a new kind of acid (low pH) inducible promoter for metabolic engineering of *A. niger*. The promoter could be provided as a regulation tool for dynamic control of fermentation, which promotes gene expression naturally as the cells finish biomass growing and begin to synthesis product.

SUMMARY OF THE INVENTION

In order to solve the above problems, the invention provides a promoter induced expression in acidic conditions. By means of the technical solutions of the invention, the cell-growth-stage and acid-producing-stage of acid fermentation by *A. niger* can be naturally set apart according to pH value, it would be useful of a low pH induced promoter for gene expression only at acid-producing-stage. The promoter provides an effective method and new thought for organic acids production by fungi or other fermentation requiring low pH.

In one aspect, the invention provides a promoter induced in acidic conditions. The promoter has a nucleotide sequence shown in SEQ ID NO. 1, or has a nucleotide sequence which is at least 90% homologous with SEQ ID NO. 1, or alternatively has a nucleotide sequence obtained from SEQ ID NO. 1 by base insertion and/or deletion, which has the same ability to promote or regulate gene expression as SEQ ID NO. 1.

In an embodiment, the promoter has the nucleotide sequence of SEQ ID NO. 1, named as Pgas.

In an embodiment, the acidic condition(s)/low pH means an acid environment that pH value is approximately equal to 2.0.

In a preferable embodiment, the acidic condition(s)/low pH means an acid environment of pH value is less than or equal to 2.0.

In another aspect, the invention also provides use of the promoter on gene expression regulation.

In an embodiment, the use comprises transforming an expression cassette containing the promoter into fungi, culturing the fungi in an acidic condition, and connecting the promoter of the expression cassette to the heterogenous nucleotide sequence such that the hegerogenous nucleotide sequene is regulated by the promoter.

In still other aspect, the invention provides an expression cassette containing the promoter.

In a preferable embodiment, the expression cassette contains the promoter, a heterogeneous nucleotide sequence effectively connected with the promoter, and a 3' transcription terminator.

In further still other aspect, the invention provides a transgenic strain containing the promoter.

In a preferable embodiment, the transgenic strain is obtained by transforming an expression cassette containing the promoter, a heterogenous nucleotide sequence and a terminator in sequence into a host cell.

In a more preferable embodiment, the host cell is selected from the group consisting of bacteria, algae, fungi, yeast, plants, insects and animal cells.

In an embodiment, the transgenic strain is constructed by the following the steps: (1) obtaining an acid-induced promoter (named Pgas) by synthesizing or PCR amplification, and constructing a recombinant plasmid by connecting the promoter, the heterogenous gene sequence (the gene to be regulated), and a terminator, Ttrp into an expression vector; (2) obtaining an expression cassette containing the promoter, the heterogenous gene sequence and the terminator in sequence by amplification of the recombinant plasmid, and transforming the expression cassette into host cells and screening for positive clones, namely, the transgenic strain.

In an embodiment, the host is *A. niger* and the heterogenous gene is GFP.

In another embodiment, the *A. niger* strain is H915-1.

By means of the above technical solutions, the invention has the following advantages: the invention obtains a promoter induced in acidic conditions (low pH) from *A. niger* successfully, and provides a method for inducing gene expression in acidic conditions. The invention provides a useful tool for metabolic engineering of *A. niger* for organic acid fermentation or fermentation of other products in low pH conditions.

DESCRIPTION OF THE PREFERRED EMBODIMENTS

Figure 1:
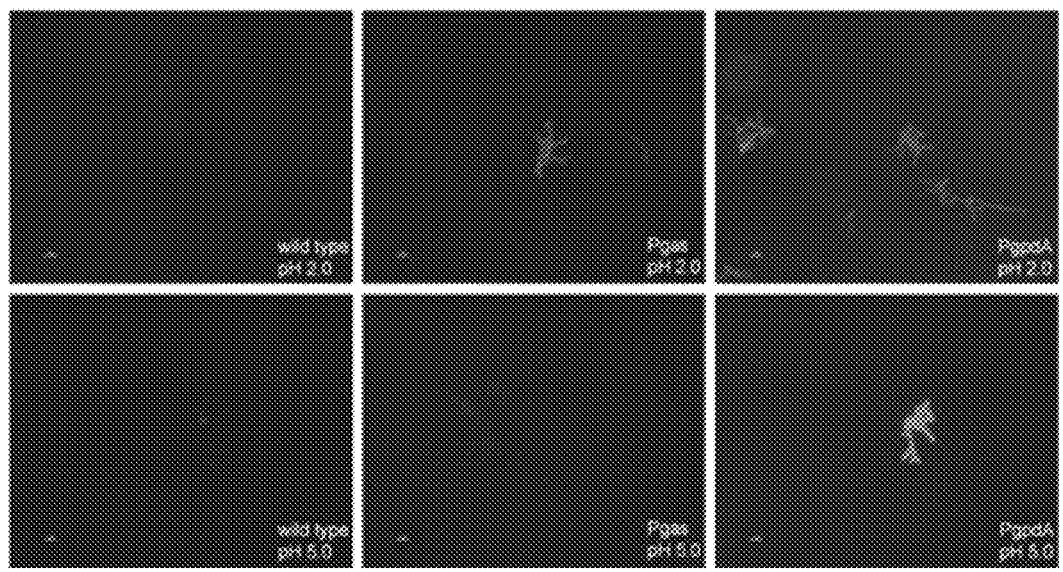
FIG. 1 shows GFP expression under the Pgas and PgpdA promoters in *A. niger* hyphae at different pH.

The invention will be further illustrated in more detail with reference to accompanying drawings. It is noted that, the following embodiments only are intended for purposes of illustration and are not intended to limit the scope of the invention.

Embodiment 1

Genome Extraction from *A. niger*

Conidia of *A. niger* ($1\times10^6$) were inoculated in 100 mL malt extract liquid medium (3% malt extract and 0.5% tryptone) at 35° C. and 250 r/min for 48 h. The mycelia were harvested with Miracloth (Calbiochem, San Diego, Calif., USA), washed with sterile water and frozen in liquid nitrogen. Tissues were ground by Liquid nitrogen grinding, and the genome DNA of *A. niger* was isolated with a DNeasy Plant Mini Kit (QIAGEN, Germantown, Md., USA).

Embodiment 2

Obtaining Promoters Induced in Acidic Conditions (by Low pH)

*A. niger* gene expression data (Accession, GSE11725) in NCBI GEO Datasets were analyzed to detect changes in mRNA levels from pH 4.5 to pH 2.5 and 4 genes was identified for increased gene expression with decreased pH value. The sequence 1500 bp upstream of the start codon ATG was analyzed using Neural Network Promoter Prediction software (version 2.2) (www.fruitfly.org/seq_tools/promoter.html) and all can be identified with a transcription start site, and the predicted promoters were named as Pgas, PpatI, Ppth, and Paat.

Pgas was amplified from the *A. niger* genome using the primers gas-F (SEQ ID NO.2) and gas-R (SEQ ID NO.3) with restriction sites Eco RI and Sma I at the 5' and 3' ends, respectively. PpatI was amplified from the *A. niger* genome using the primers pat-F (SEQ ID NO.4) and pat-R (SEQ ID NO.5) with restriction sites Sac I and Bam HI at the 5' and 3' ends, respectively. Ppth was amplified from the *A. niger* genome using the primers pth-F (SEQ ID NO.6) and pth-R (SEQ ID NO.7) with restriction sites Sac I and Bam HI at the 5' and 3' ends, respectively. Paat was amplified from the *A. niger* genome using the primers aat-F (SEQ ID NO.8) and aat-R (SEQ ID NO.9) with restriction sites Eco RI and Bam HI at the 5' and 3' ends, respectively.

Primer sequences were as follows:

```
gas-F (SEQ ID NO. 2):
GAATTCCTGCTCTCTCTCTGCTCTCTTTCT gas-R (SEQ ID NO. 3):
CCCGGGGTGAGGAGGTGAACGAAAGAAGAC pat-F (SEQ ID NO. 4):
GAGCTCTTAGGAAACCTACCATCCATCGTA pat-R (SEQ ID NO. 5):
GGATCCTGTGCTGCTTGACTGGACGTTCA
```

-continued
```
pth-F (SEQ ID NO. 6):
GAGCTCTATGTGTCACGAGTTAGAAAGGA pth-R (SEQ ID NO. 7):
GGATCCGTGGCCTACATGCTCTGAAACA aat-F (SEQ ID NO. 8):
GAATTCCGCTATCTCCATCTGATAGCCATA aat-R (SEQ ID NO. 9):
GGATCCGATTGCTTGTCGATTATACAGCGT
```

Embodiment 3

Construction of Expression Cassette of Promoters Induced in Acidic Conditions

GFP (SEQ ID NO.10) was synthesized with coden optimization and contained Bam HI and Pst I restriction sites at the 5' and 3' ends, respectively. Trp terminator (Ttrp) was PCR amplified with primers Ttrp-F (SEQ ID NO.11) and Ttrp-R (SEQ ID NO.12) using pAN7-1 as a template, and restriction sites Pst I and Hin dIII was added to the 5' and 3' ends, respectively. Ttrp was digested with Hin dIII and Pst I, GFP was digested with Bam HI and Pst I, and the two sequence were ligated to pUC18 digested with the same enzyme, and pGT was obtained. GFP-Ttrp was amplified with the primers GFP-F1 (SEQ ID NO.13) and Ttrp-R using pGT as a template and reversely connected to pMD19-T vector (Takara, Tokyo, Japan) to generate pMD-GFP-Ttrp. Pgas and pMD-GFP-Ttrp were digested with Eco RI and Sma I and connected to generate the Pgas-GFP-Ttrp expression vector. For co-transformation, the Pgas-GFP-Ttrp expression cassette was obtained by PCR with the primers gas-F and Ttrp-R. With the similar method, the PpatI-GFP-Ttrp, Paat-GFP-Ttrp, Ppth-GFP-Ttrp expression cassettes containing the PpatI, Ppth, Paat promoters respectively were obtained.

For co-transformation, the hygromycin resistant cassette, PgpdA-hph-Ttrp, was obtained by PCR with the primers PgpdA-F (SEQ ID NO.14) and Ttrp-R-2 (SEQ ID NO.15) using pAN7-1 as a template.

Primers:

```
Ttrp-F (SEQ ID NO. 11):
CTGCAGAGATCCACTTAAACGTTACTGAAATC

Ttrp-R (SEQ ID NO. 12):
AAGCTTTCGAGTGGAGATGTGGAGTGG

GFP-F1 (SEQ ID NO. 13):
GATCCATGGTGAGCAAGG

PgpdA-F (SEQ ID NO. 14):
CAATTCCCTTGTATCTCTACACACAG

Ttrp-R-2 (SEQ ID NO. 15):
TCGAGTGGAGATGTGGAGTGG
```

Embodiment 4

Preparation and Transformation of Protoplast of *A. niger*

Conidia ($3\times10^5$/mL) were inoculated in ME medium overnight at 200 r/min under 30° C. The mycelium was harvested via filtration through Miracloth and washed with sterile water. Protoplastation was achieved in the presence of lysing enzymes in KMC (0.7M KCl, 50 mM $CaCl_2$, 20 mM Mes/NaOH, pH 5.8) for 3 h at 1000 rpm under 37° C. The protoplasts were filtered through Miracloth and collected via centrifugation at 1,000 rpm under 4° C. for 10 min and subsequently washed twice with the same volume STC (1.2 M sorbitol, 10 mM Tris/HCl, 50 mM CaCl$_2$, pH 7.5), and finally resuspended in 100 μL STC and directly used for transformation. Ten micrograms of expression cassette (obtained in Example 3) was mixed with 100 μL STC solution containing at least $10^7$ protoplasts and 330 μL polyethylene glycol (PEG) solution (25% PEG 6000, 50 mM CaCl$_2$, 10 mM Tris/HCl, pH 7.5) and kept on ice for 20 min. After mixing with an additional 2 mL PEG solution and incubating at room temperature for 10 min, the protoplast mixture was diluted with 4 mL STC. The aliquots were mixed with 4 mL liquid top agar warmed to 48° C., spread on bottom agar containing 150 μg/mL hygromycin, and incubated at 35° C. for 4-7 days until clones appeared. All transformants were purified three times via single-colony isolation on the selection medium. The correct integration was verified with PCR analysis by using specific genomic primers.

Embodiment 5

Conidia ($3\times10^5$/mL) of *A. niger* transformants were inoculated in LBL medium with different pH (pH at 2.0, 3.0, 4.0 and 5.0) and cultured at 35° C. at 120 r/min for 24 h. The samples were checked under a microscope using blue light to detect the fluorescent of GFP. Wild-type H915-1 did not show fluorescence at both pH 2.0 and pH 5.0. The PgpdA transformant showed extremely strong fluorescence intensity at pH 5.0, and strong fluorescence at pH 2.0. The Pgas transformant showed minimal GFP expression at pH 5.0, but enhanced fluorescence intensity at pH 2.0 (as shown in FIG. 1.), this indicated that the promoter acts as an acid-enhanced cis-acting element Relative GFP Fluorescence Strength The *A. niger* transformants were cultured at 35° C. for additional 48 h. The pellets were harvested and washed twice with WS buffer (100 mM Tris, pH 7.0) and dried with filter paper immediately. The pellets were transferred to the MP Lysing Matrix C (MP Biomedicals, Heidelberg, Germany) and the mycelia were disrupted for 3×30 s at 5 m/sec using a FastPrep-24 (MP Biomedicals, New York, N.Y., USA). After centrifugation at 12,000 rpm and 4° C. for 10 min, the supernatant was obtained as a protein sample. The total protein concentration was determined using the BCA Protein Assay Kit. The protein concentration of each sample was diluted to 50 μg/mL and the exact protein concentration (A) was determined. The Cytation 3 Cell Imaging Multi-Mode Reader was used to detect fluorescence with an excitation wavelength of 485 nm and emission wavelength of 535 nm, and the fluorescence intensity was labeled B. The standardized fluorescent intensity was estimated as B divided by A.

Figure 2:
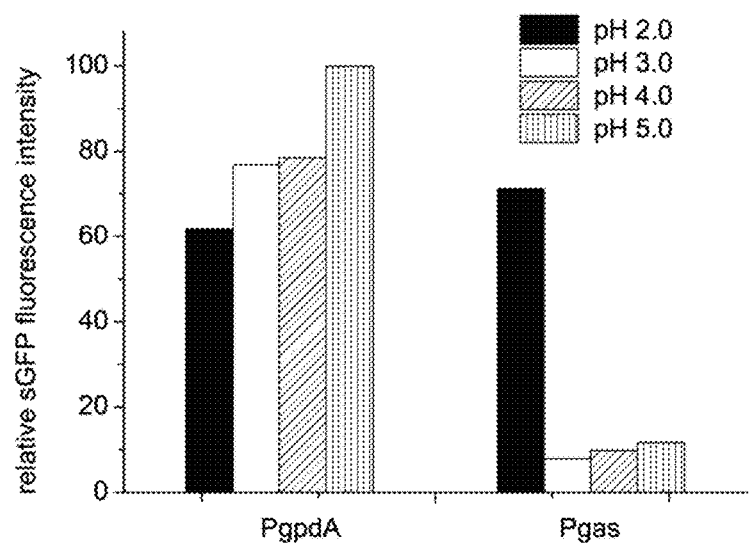
FIG. 2 shows GFP fluorescence intensity of transformants at different pH, wherein gpdA, pth, aat, patI and gas represent transformants with GFP gene expression controlled by PgpdA, Ppth, Paat, PpatI and Pgas respectively.

As shown in FIG. 2, the fluorescence intensity of PgpdA was strong at different pH, and was set as 100% at pH 5.0. The fluorescence of PgpdA decreased from pH 5.0 to pH 2.0. Nevertheless, Pgas showed little fluorescence at pH 3.0, 4.0, and 5.0, but enhanced fluorescence at pH 2.0, which was stronger than that of PgpdA at pH 2.0, but weaker than that of PgpdA at pH 5.0. The PpatI, Ppth and Paat transformants did not show significant inducement at low pH.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A method of regulating fungal gene expression comprising:

providing an expression cassette comprising an isolated promoter consisting of the nucleotide sequence set forth in SEQ ID NO: 1, the isolated promoter being operably linked to a nucleotide sequence encoding a protein of interest;

transforming the expression cassette into *Aspergillus niger*; and culturing *Aspergillus niger* under an acid condition to induce the isolated promoter.

* * * * *

SEQUENCE LISTING

```
<160> NUMBER OF SEQ ID NOS: 15

<210> SEQ ID NO 1
<211> LENGTH: 1493
<212> TYPE: DNA
<213> ORGANISM: Artificial Sequence
<220> FEATURE:
<223> OTHER INFORMATION: DNA sequence of promoter Pgas

<400> SEQUENCE: 1
ctgctctctc tctgctctct ttctgcgctc tctgtgtcgg cactaacccc gaatggggcg      60
ggtatcggca gtccgacgga tctccggggg ccgcacgtcc agcgccgatc gttactcaac     120
cgagcagagg agagagagca gtgagcagtg gtgtcaccga ccataaaaat gcttgcttct     180
gcccatccag ccatcagttg tccagtctgc tccattgtgt gccagtctcg cccccaaggc     240
cgcgcatctg aaaccaaccg gttgggtgaa atcagccggc gggtggcacc cgagcggcca     300
ctggctggga tcatcgcccg caacgcgtca acagcaatca aacgaaggat gcgaaattat     360
tcagcgggcg gttcctttcc aattttttccc cgttcctgtc agcatgtcta ctctatcata     420
ctgtaacatt attatattgt gattattttt attctgggtg atgtgtccac tggaccgcac     480
gtggaatgaa gattttcctt ccctcgggac gagaaaccat ggcgcagttg gtgttgtgtg     540
cgtgtgtgtg cgtgtcggtt gtccgaaaat cgccctaaac tccgaggcac gcaccatttg     600
ccattaattc ccttgcgatt gatttctgcc tgtccctgcg acccttttgtg acccttttgtg     660 acccttttgac cctggattca ggggcttggt ggactcatag cgatggggat agggacttt      720
```

-continued

```
gacccttttg acccttttgac cctcccattt tccctggcct aagtacgctg tagtcgtaat    780
tatagaaaga atcttgcgtg gactggggca aaagggaac agaacttatc catgtccgag     840
cagcgatcgg ccagtcacca agccggctgg atccgagacc cgctacgtgg gaactcccaa    900
gagtcgttaa gcaaagccaa gagatcagcc aagatgtcgc tcacgagcct aattgctgga    960
ttgccatatc gcttgtcgtt gtaccatcgc gtaagatttt atcattgttt ctgggggctg    1020
tcagctagtc taaaacgtac tcctcaaacc agagaggctg atgatgctga tgatgggcct    1080 ccaccccca aattggtagc gccgttccat gagaggccca gtctctctct gcccgtcctc     1140
gaccattgtt tggcccagca ctgacacaac cttcaggggg ggccaatgga cgtattccgt    1200
aggcagcagg caaatgcggc cctaagaact ccccaactaa taagagtcca gactagcaaa    1260
ggttcgcctc gccggtctcc atctcttcct tcttagtcct cccatttcct ccctcccact    1320
tggtctctcg ctccagattt cctttcttct ttcatccatc ccatcttgta tccttttgct    1380
tagccttttt gtttggtttt cttcctctcg ttaaccacca cattcgctct atcttaatac    1440
aaaccaccca cactcgttct atagcatctg tcttctttcg ttcacctcct cac           1493
```

```
<210> SEQ ID NO 2
<211> LENGTH: 30
<212> TYPE: DNA
<213> ORGANISM: Artificial Sequence
<220> FEATURE:
<223> OTHER INFORMATION: DNA sequence of primer gas-F

<400> SEQUENCE: 2
gaattcctgc tctctctctg ctctctttct                                      30

<210> SEQ ID NO 3
<211> LENGTH: 30
<212> TYPE: DNA
<213> ORGANISM: Artificial Sequence
<220> FEATURE:
<223> OTHER INFORMATION: DNA sequence of primer gas-R

<400> SEQUENCE: 3 cccgggggtga ggaggtgaac gaaagaagac                                     30

<210> SEQ ID NO 4
<211> LENGTH: 30
<212> TYPE: DNA
<213> ORGANISM: Artificial Sequence
<220> FEATURE:
<223> OTHER INFORMATION: DNA sequence of primer pat-F

<400> SEQUENCE: 4
gagctcttag gaaacctacc atccatcgta                                      30

<210> SEQ ID NO 5
<211> LENGTH: 29
<212> TYPE: DNA
<213> ORGANISM: Artificial Sequence
<220> FEATURE:
<223> OTHER INFORMATION: DNA sequence of primer pat-R

<400> SEQUENCE: 5
ggatcctgtg ctgcttgact ggacgttca                                       29

<210> SEQ ID NO 6
<211> LENGTH: 29
<212> TYPE: DNA
<213> ORGANISM: Artificial Sequence
```

```
<220> FEATURE:
<223> OTHER INFORMATION: DNA sequence of primer pth-F

<400> SEQUENCE: 6
gagctctatg tgtcacgagt tagaaagga                              29

<210> SEQ ID NO 7
<211> LENGTH: 28
<212> TYPE: DNA
<213> ORGANISM: Artificial Sequence
<220> FEATURE:
<223> OTHER INFORMATION: DNA sequence of primer pth-R

<400> SEQUENCE: 7
ggatccgtgg cctacatgct ctgaaaca                               28

<210> SEQ ID NO 8
<211> LENGTH: 30
<212> TYPE: DNA
<213> ORGANISM: Artificial Sequence
<220> FEATURE:
<223> OTHER INFORMATION: DNA sequence of primer aat-F

<400> SEQUENCE: 8
gaattccgct atctccatct gatagccata                             30

<210> SEQ ID NO 9
<211> LENGTH: 30
<212> TYPE: DNA
<213> ORGANISM: Artificial Sequence
<220> FEATURE:
<223> OTHER INFORMATION: DNA sequence of primer aat-R

<400> SEQUENCE: 9
ggatccgatt gcttgtcgat tatacagcgt                             30

<210> SEQ ID NO 10
<211> LENGTH: 720
<212> TYPE: DNA
<213> ORGANISM: Artificial Sequence
<220> FEATURE:
<223> OTHER INFORMATION: DNA sequence of primer GFP

<400> SEQUENCE: 10
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctgggcac    420 aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actcacggca tggacgagct gtacaagtaa   720

<210> SEQ ID NO 11
```

```
<211> LENGTH: 32
<212> TYPE: DNA
<213> ORGANISM: Artificial Sequence
<220> FEATURE:
<223> OTHER INFORMATION: DNA sequence of primer Ttrp-F

<400> SEQUENCE: 11
ctgcagagat ccacttaaac gttactgaaa tc                                     32

<210> SEQ ID NO 12
<211> LENGTH: 27
<212> TYPE: DNA
<213> ORGANISM: Artificial Sequence
<220> FEATURE:
<223> OTHER INFORMATION: DNA sequence of primer Ttrp-R

<400> SEQUENCE: 12
aagctttcga gtggagatgt ggagtgg                                           27

<210> SEQ ID NO 13
<211> LENGTH: 18
<212> TYPE: DNA
<213> ORGANISM: Artificial Sequence
<220> FEATURE:
<223> OTHER INFORMATION: DNA sequence of primer GFP-F1

<400> SEQUENCE: 13
gatccatggt gagcaagg                                                     18

<210> SEQ ID NO 14
<211> LENGTH: 26
<212> TYPE: DNA
<213> ORGANISM: Artificial Sequence
<220> FEATURE:
<223> OTHER INFORMATION: DNA sequence of primer PgpdA-F

<400> SEQUENCE: 14
caattccctt gtatctctac acacag                                            26

<210> SEQ ID NO 15
<211> LENGTH: 21
<212> TYPE: DNA
<213> ORGANISM: Artificial Sequence
<220> FEATURE:
<223> OTHER INFORMATION: DNA sequence of primer Ttrp-R-2

<400> SEQUENCE: 15
tcgagtggag atgtggagtg g                                                 21
```